United States Patent
Xie et al.

(10) Patent No.: US 10,570,410 B2
(45) Date of Patent: Feb. 25, 2020

(54) ARTIFICIAL SALT TOLERANT PROTEIN, ITS SYNTHETIC METHOD AND CODING GENE THEREOF AND USE OF SAID CODING GENE

(71) Applicant: Tianjin Agricultural University, Tianjin (CN)

(72) Inventors: Xiaodong Xie, Tianjin (CN); Yao Zhan, Tianjin (CN); Shoujun Sun, Tianjin (CN); Gaoyi Cao, Tianjin (CN); Ming Li, Tianjin (CN); Bo Ding, Tianjin (CN); Xiaoqiang Chen, Tianjin (CN)

(73) Assignee: TIANJIN AGRICULTURAL UNIVERSITY, Tianjin (CN)

( * ) Notice: Subject to any disclaimer, the term of this patent is extended or adjusted under 35 U.S.C. 154(b) by 0 days.

(21) Appl. No.: 15/785,707

(22) Filed: Oct. 17, 2017

(65) Prior Publication Data
US 2018/0223306 A1    Aug. 9, 2018

(30) Foreign Application Priority Data
Feb. 7, 2017 (CN) .......................... 2017 1 0067935

(51) Int. Cl.
| | | |
|---|---|---|
| *C12N 15/82* | (2006.01) | |
| *C07K 14/415* | (2006.01) | |
| *C12N 15/70* | (2006.01) | |
| *C40B 40/08* | (2006.01) | |
| *C12N 15/74* | (2006.01) | |

(52) U.S. Cl.
CPC ........ *C12N 15/8273* (2013.01); *C07K 14/415* (2013.01); *C12N 15/70* (2013.01); *C12N 15/821* (2013.01); *C12N 15/8209* (2013.01); *C40B 40/08* (2013.01); *C12N 15/743* (2013.01)

(58) Field of Classification Search
None
See application file for complete search history.

(56) References Cited

PUBLICATIONS

NCBI Reference Sequence: XP 010045838.1, late embryogenesis abundant protein D-34 [Eucalyptus grandis], Oct. 25, 2016, p. 1-2. (Year: 2016).*
Liu et al., Genome-wide Identification and Characterization of a Dehydrin Gene Family in Poplar (*Populus trichocarpa*). Plant Mol Biol Rep (2012) 30:848-859 (Year: 2012).*
Kadlecova et al., Comparative study on the in vitro cytotoxicity of linear, dendritic, and hyperbranched polylysine analogues. Biomacromolecules. Oct. 8, 2012;13(10):3127-37. (Year: 2012).*
Hunault et al., Lea protein data base, 2007. http://forge.info.univ-angers.fr/-gh/Leadb/index.php?action=0&mode=0 (Year: 2007).*

\* cited by examiner

*Primary Examiner* — Chritopher M Babic
*Assistant Examiner* — Arthur S Leonard
(74) *Attorney, Agent, or Firm* — Mayer & Williams, PC

(57) ABSTRACT

This invention relates to an artificial salt tolerant protein NLEA with the amino acid sequence shown in SEQ ID No.1 and a synthetic method of salt tolerant protein NLEA comprising the steps of retrieving different types of LEA proteins from LEA database; making multiple sequence alignment on different types of LEA proteins to obtain conserved short peptides; selecting hydrophilic short peptides with a hydrophilicity index higher than 3.5 from conserved short peptides; arranging and splicing hydrophilic short peptides in the order of isoelectric point size from large to small, to obtain salt tolerant protein NLEA. This invention involves bioinformatics analysis by retrieving different LEA conserved amino acid sequences of LEA protein data. Physical properties are analyzed to find short peptides of high hydrophilicity, and such short peptides are arranged in the order of isoelectric point size and spliced to get a new hydrophilic amino acid sequence.

11 Claims, 3 Drawing Sheets
Specification includes a Sequence Listing.

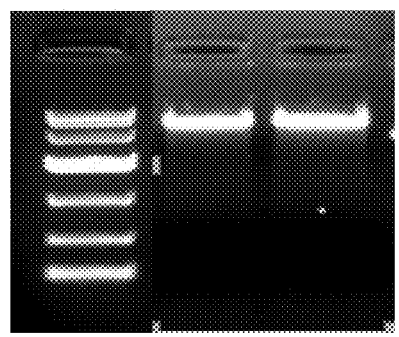
Figure 1
SEQ ID NO:1
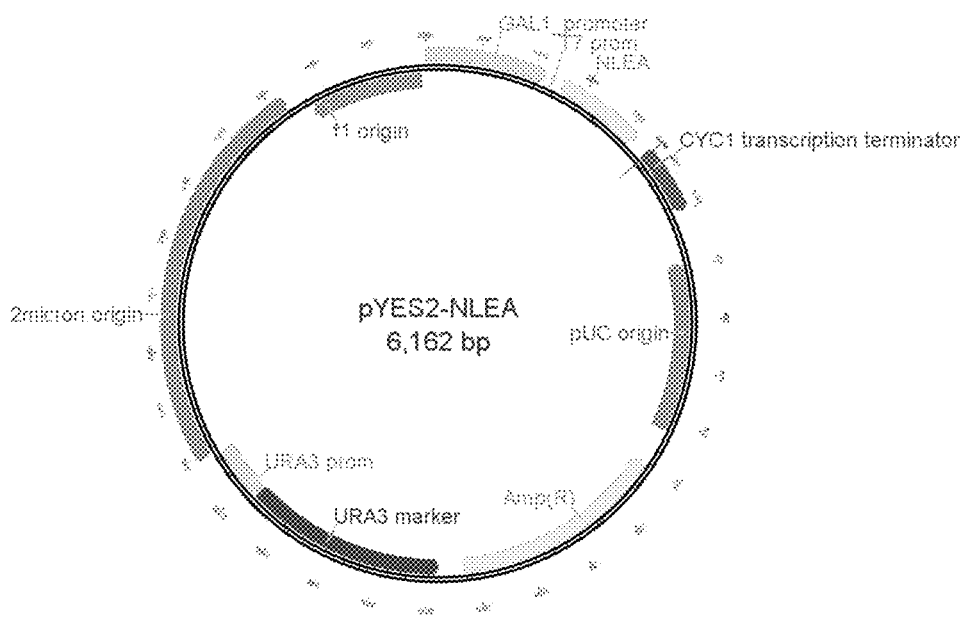
Figure 2
Figure 3

Cultivating for 11 days        Cultivating for 20 days

ARTIFICIAL SALT TOLERANT PROTEIN, ITS SYNTHETIC METHOD AND CODING GENE THEREOF AND USE OF SAID CODING GENE

TECHNICAL FIELD

This invention belongs to genetic engineering field, specifically relates to an artificial salt tolerant protein, its synthetic method and coding gene thereof and use of said coding gene.

BACKGROUND ART

At present, $4\times10^3\sim9\times10^3$ hm$^2$ land is affected by salinization in the world, and $2.6\times10^7 11$ m$^2$ in China, wherein, around $6.6\times10^3$ hm$^2$ land is cultivated land. Land salinization has become an important factor affecting crop growth. Along with the industrial development, quality of irrigation water is degrading, and soil salinization is increasingly exacerbated. Thus, salinization treatment, comprehensive development of saline land, improvement of salt tolerance of plants, and utilization of saline water resource have great impact on plant growth.

Breeding of salt tolerant crops is an effective approach of saline land development and utilization. Main methods of salt tolerant crop breeding in prior art include: domestication of wild salt tolerant plants, traditional breeding, distant hybridization of crops and wild sibling species, mutation selection, genetic engineering breeding, and etc. However, due to insufficient understanding of the biochemical foundations of salt tolerance of plants, salt tolerant crop with practical significance has not been obtained so far.

As molecular biology develops rapidly, the physiological and biochemical mechanisms of plant salt tolerance become explicit, which makes clone of genes relating to plant salt tolerance possible. For example, the patent with the publication number of CN 103204915 B discloses salt tolerance related protein IbEST of sweet potato, its coding gene and its use thereof, wherein said IbEST protein is sourced from sweet potato and the salt tolerance of said protein in other breeds is unknown. For one more example, the patent with the publication number of CN 102796713 B publishes salt tolerance related protein and gene of plants and their application as selection marker, and specifically discloses a plant salt tolerance related protein named GmVP, wherein salt tolerance is shown when said salt tolerance related protein is transcribed into endogen or dicotyledon. However, plant sourced salt tolerant protein or gene has species restriction, and thus their application is limited. However, in prior art, no artificial salt tolerant protein has been reported, and there is no report on artificial salt tolerant protein in transgenic microorganism.

SUMMARY OF THE INVENTION

In view of above, this invention aims to provide an artificial salt tolerant protein, its synthetic method and coding gene thereof and use of said gene, so that said artificially-synthetic salt tolerant protein can improve the salt tolerance of its microorganism hosts.

To achieve above invention purpose, this invention provides the following technical solutions:

This invention provides an artificial salt tolerant protein NLEA, possessing the amino acid sequence shown as SEQ ID NO:1.

This invention provides a synthetic method of said salt tolerant protein NLEA, comprising the following steps:
1) retrieving different types of LEA proteins from LEA database;
2) making multiple sequence alignment on the different types of LEA proteins retrieved in step 1) to obtain conserved short peptides;
3) selecting hydrophilic short peptides with a hydrophilicity index higher than 3.5 from the conserved short peptides obtained in step 2);
4) arranging and splicing the hydrophilic short peptides obtained in step 3) in the order of isoelectric point size from large to small, to get salt tolerant protein NLEA.

Preferably, the hydrophilicity index mentioned in step 3) is calculated by using the Formula I below:

$$\text{hydrophilicity index} = \frac{\sum_{i=1}^{n} f(i)}{n} \qquad \text{formula I}$$

f(i) is the hydrophilicity number of single amino acid; n=11.

Preferably, clustering analysis is made on said conserved short peptides before selecting the hydrophilic short peptides in said step 3), to get conserved short peptides clustering different branches.

This invention provides coding gene nlea of said salt absorbent protein, possessing nucleotide sequence shown as of SEQ ID NO:2.

This invention also provides a recombinant expression vector comprising said coding gene.

Preferably, said recombinant expression vector is pYES2-nlea.

This invention provides a host comprising said recombinant expression vector.

Preferably, said host comprises *S. cerevisiae*, *E. coli* or *Agrobacterium*.

This invention also provides use of said coding gene as selection marker in microorganism transgenic cell culture and model plant *Arabidopsis thaliana*.

This invention provides a synthetic method of said salt tolerant protein NLEA, comprising the following steps: 1) retrieving different types of LEA proteins from LEA database; 2) making multiple sequence alignment of the different types of LEA proteins retrieved in step 1) to obtain conserved short peptides; 3) selecting hydrophilic short peptides with a hydrophilicity index higher than 3.5 from the conserved short peptides obtained in step 2); 4) arranging and splicing the hydrophilic short peptides obtained in Step 3) in the order of isoelectric point size from large to small, to obtain salt tolerant protein NLEA. This invention involves bioinformatics analysis by means of retrieving different LEA conserved amino acid sequences of LEA protein data; specifically, physical properties such as hydrophilicity, isoelectric point and electric charge polarity are analyzed to find short peptides of high hydrophilicity, and such short peptides are arranged in the order of isoelectric point size and then spliced to get a new hydrophilic amino acid sequence consisting of 110 amino acid residues. The method provided in the invention is characterized by simple construction steps, standard and reliable approach, and not restricted by species. The salt tolerant protein constructed in this invention can produce high salt tolerance after being transferred into microorganism host cells. It's demonstrated by combining embodiments that, the salt tolerance of *S. cerevisiae* with NLEA transferred in sodium chloride solution with molar concentrations of 0.5 mol/L and 0.6 mol/L is significantly different from the salt tolerance of the control group, and the highest salt tolerance of *S. cerevisiae* with NLEA transferred is up to 0.8 mol/L NaCl. The salt tolerant protein constructed in this invention can also produce high salt tolerance after being transferring into model plant *Arabidopsis thaliana*. It's demonstrated by combining embodiments that, the salt tolerance of *Arabidopsis thaliana* with NLEA transferred in sodium chloride solution with molar concentrations of 100 m mol/L is significantly different from that of the control group. Transgenic plants normally grow, and non-transgenic plants become white and die.

This invention provides an artificial salt tolerant protein NLEA with the amino acid sequence shown as SEQ ID NO:1. Said artificial salt tolerant protein NLEA has high hydrophilicity. On the one hand, proteins of high hydrophilicity can reduce hydraulic potential of cells so that they can better absorb water from the environment, on the other hand, enhancement of water content in cells helps to reduce concentrations of ions and thus reduce the toxic effects of ions. Thus, said salt tolerant protein NLEA can improve salt tolerance of cells.

DESCRIPTION OF DRAWINGS

FIG. 1 shows the principle of In-Fusion technology;

FIG. 2 is a diagram of agarose gel electrophoresis of the vectors after double digestion in example 2;

FIG. 3 shows an expression vector containing salt tolerant coding gene nlea in example 3;

EMBODIMENTS

Figure 4:
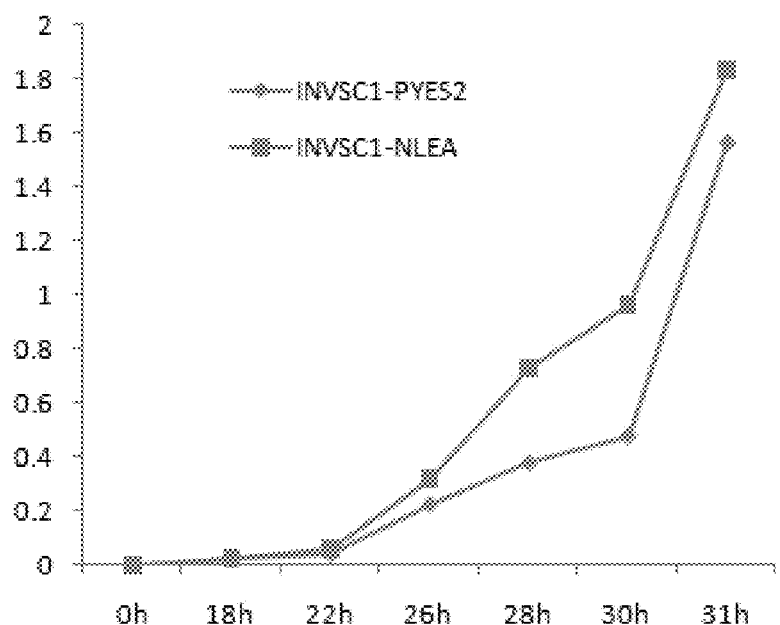
FIG. 4 shows the growth curve of *S. cerevisiae* under salt stress in example 5.

This invention provides an artificial salt tolerant protein NLEA, possessing the amino acid sequence shown as SEQ ID NO:1.

This invention provides a synthetic method of said salt tolerant protein NLEA, comprising the following steps:
1) retrieving different types of LEA proteins from LEA database;
2) making multiple sequence alignment on the different types of LEA proteins retrieved in step 1) to obtain conserved short peptides;
3) selecting hydrophilic short peptides with a hydrophilicity index higher than 3.5 from the conserved short peptides obtained in step 2);
4) arranging and splicing the hydrophilic short peptides obtained in step 3) in the order of isoelectric point size from large to small, to get salt tolerant protein NLEA.

In this invention, different types of LEA proteins are retrieved from LEA database.

In this invention, said LEA database is preferably Late Embryogenesis Abundant Proteins DataBase. The quantity of said different types of LEA proteins is preferably 1,643 LEA proteins sourced from different plants.

After obtaining different types of LEA proteins, multiple sequence alignment of said proteins is made to obtain conserved short peptides.

In this invention, the tool of said multiple sequence alignment is bioinformatics software BioEdit preferably. Said method of multiple sequence alignment is subject to no special restriction, and any common multiple sequence alignment methods known by a person skilled in the art can be used.

In this invention, the length of said conserved short peptides is preferably 11 amino acids. When the length of conserved short peptides is greater than 11, the conserved short peptides whose whole hydrophilicity is higher will be selected preferably in the invention.

After getting the conserved short peptides, hydrophilic short peptides with a hydrophilicity index higher than 3.5 are selected from said conserved short peptides.

In this invention, said hydrophilicity index is preferably calculated by using formula I below:

$$\text{hydrophilicity index} = \frac{\sum_{i=1}^{n} f(i)}{n} \quad \text{formula I}$$

f(i) is the hydrophilicity number of single amino acid; n=11.

In this invention, said hydrophilicity numbers of single amino acid are shown in Table 1.

TABLE 1

| hydrophilicity numbers of common amino acids | | | |
|---|---|---|---|
| Abbreviation of amino acid | Hydrophilicity number | Abbreviation of amino acid | Hydrophilicity number |
| Arg (R) | 4.5 | Gly (G) | 0.4 |
| Lys (K) | 3.9 | Ser (S) | 0.8 |
| Asn (N) | 3.5 | Thr (T) | 0.7 |
| Asp (D) | 3.5 | Ala (A) | −1.8 |
| Gln (Q) | 3.5 | Met (M) | −1.9 |
| Glu (E) | 3.5 | Cys (C) | −2.5 |
| His (H) | 3.2 | Phe (F) | −2.8 |
| Pro (P) | 1.6 | Leu (L) | −3.8 |
| Tyr (Y) | 1.3 | Val (V) | −4.2 |
| Trp (W) | 0.9 | Ile (I) | −4.5 |

In this invention, preferably, before selecting the hydrophilic short peptides, clustering analysis is made on said conserved short peptides to obtain short peptides of different branches. The purpose of said clustering analysis is to select conserved short peptides composed of different amino acids.

In this invention, preferably, the tool of said clustering is bioinformatics software MEGA6. The method of said clustering is subject to no special restriction, and any common clustering methods known by a person skilled in the art can be used.

After obtaining the hydrophilic short peptides, said hydrophilic short peptides are arranged in the order of isoelectric point size from large to small, and then spliced to obtain salt tolerant protein NLEA.

In this invention, molecular weights, isoelectric points and electric charge polarity of said hydrophilic short peptides are analyzed. Preferably, the said tool of analysis is online software SMART.

In this invention, the properties of part of said hydrophilic short peptides such as molecular weight, isoelectric point and electric charge polarity are shown in Table 2.

TABLE 2

List of properties of hydrophilic short peptides such as molecular weight, isoelectric point and electric charge polarity

| Hydrophilic short peptides | Number of amino acids | Molecular weight | Iso-electric point | Molecular formula | Total number of atoms | Average hydro-philicity index |
|---|---|---|---|---|---|---|
| KKRRRKERKEK | 11 | 1541.8 | 11.59 | $C_{64}H_{124}N_{28}O_{16}$ | 232 | −4.045 |
| KRRRKERKEKK | 11 | 1541.8 | 11.59 | $C_{64}H_{124}N_{28}O_{16}$ | 232 | −4.045 |
| EKRKKKKKEKK | 11 | 1457.8 | 10.47 | $C_{64}H_{124}N_{22}O_{16}$ | 226 | −3.882 |
| KRKKKKKEKKE | 11 | 1457.8 | 10.47 | $C_{64}H_{124}N_{22}O_{17}$ | 226 | −3.882 |
| RKKKKKEKKEK | 11 | 1457.8 | 10.47 | $C_{64}H_{124}N_{22}O_{18}$ | 226 | −3.882 |
| EKKKKKEKKKK | 11 | 1429.8 | 10.3 | $C_{64}H_{124}N_{20}O_{16}$ | 224 | −3.827 |
| KKKKKEKKKKD | 11 | 1415.7 | 10.3 | $C_{63}H_{122}N_{20}O_{16}$ | 221 | −3.827 |
| KKKKKEKKKKD | 11 | 1571.6 | 9.4 | $C_{60}H_{106}N_{28}O_{22}$ | 216 | −3.955 |
| EEKKRRRKERK | 11 | 1542.8 | 11 | $C_{63}H_{119}N_{27}O_{18}$ | 227 | −4.009 |
| EKRKKKKEKKK | 11 | 1457.83 | 10.47 | $C_{64}H_{124}N_{22}O_{16}$ | 226 | −3.882 |

In this invention, the method of said splicing is subject to no special restriction, and any common splicing methods known by a person skilled in the art can be used.

In this invention, most amino acid residues of said salt tolerant protein NLEA are alkaline and hydrophilic amino acids, without cysteine or tryptophan, with strong hydrophilicity and conservativeness, and without complex tertiary structure.

This invention provides a coding gene nlea of said salt tolerant protein, which has the nucleotide sequence shown as SEQ ID NO:2.

In this invention, the selection method of said coding gene nlea preferably includes the following steps:

A. translating the amino acid sequence of the salt tolerant protein to nucleotide sequence in accordance with that one amino acid corresponds to one or more codons;

When one amino acid corresponds to several codons, dominant codon is selected.

Said dominant codon is determined based on the use frequencies of different codons of the same amino acid in microzyme genome in Genetic Codes database. The codon with the highest use frequency is the dominant one.

B. Adjusting said nucleotide sequence obtained by translation to exclude sequences with a GC content higher than 60%.

This invention also provides a recombinant expression vector containing said coding gene. In this invention, preferably, said recombinant expression vector is pYES2-nlea.

In this invention, the construction method of said recombinant expression vector preferably includes the following steps:

(1) taking the coding gene NLEA sequence synthesized by the company as template, conducting PCR amplification, recycling the product of PCR amplification, and obtaining PCR product;

(2) Performing double digestion on plasmid pYES2 by using SacI and EcoRI enzymes to get linearized plasmid PYES2;

(3) Connecting the gel extraction product of linearized plasmid pYES2 and the gel extraction PCR product of NLEA by means of In-Fusion reaction to get recombinant expression vector.

Said Step (1) and Step (2) are subject to no restriction in time sequence.

In this invention, the synthesized sequence of coding gene nlea is taken as template for PCR amplification. In this invention, the nucleotide sequence of the forward primer for said PCR amplification is shown as SEQ ID NO:3; the nucleotide sequence of the reverse primer for said PCR amplification is shown as SEQ ID NO:4.

In this invention, said PCR amplification system preferably includes DNA template 1 μL, 5× Phushion HF buffer 4 μL, 10 mmol/L dNTPs 0.4 μL, 10 μM gene specific primers 1 μL, Phusion DNA polymerase 0.2 μL, DMSO 0.6 μL, and the whole reaction volume is made up a deficiency to 20 μL by using water.

In this invention, preferably, said PCR amplification procedure is 98° C. 30 s, taking 98° C. 10 s, 60° C. 30 s, 72° C. 1 min as one cycle, conducting 35 cycles, and finally 72° C. 5 min.

After said PCR amplification, the PCR amplification products are reclaimed. Said reclaiming of amplification products is conducted preferably by using reagent kit. The type of said reagent kit is subject to no special restriction, and any common reagent kit for the PCR amplification products known by a person skilled in the art can be used.

In this invention, double digestion is performed on plasmid PYES2 by using SacI and EcoRI enzymes.

In this invention, the source of said SacI and EcoRI enzymes is subject to no special restriction, and any common SacI and EcoRI enzymes known to a person skilled in the art can be used. In the embodiments of this invention, said SacI and EcoRI enzymes were purchased from Beijing NEB Company.

In this invention, the source of said plasmid pYES2 is subject to no special restriction, and any common sources known by a person skilled in the art can be used. In the examples of this invention, said plasmid pYES2 was presented by China Agricultural University.

In this invention, the reaction system of said digestion is 20,000 unit/ml SacI 1 μL, EcoRI 1 μL, 10× CutSmart 2.5 μL, pYES2 5 μL; the digestion temperature is preferably 50° C., incubating for 1 h; deactivating at 65° C. for 15 min.

After obtaining plasmid pYES2 and gel extraction PCR product of NLEA, the gel extraction product of linearized plasmid pYES2 and the gel extraction PCR product of nlea are connected to get recombinant expression vector.

In this invention, said connection is preferably performed by means of In-Fusion reaction. The principle of said In-Fusion reaction is 15 homologous bases at the ends of inserted sections and the linearized vector (see FIG. 1).

In this invention, the system of said In-Fusion reaction is as below: the linearized vector pYES2 3 μL, PCR product 5 μL, 5× In-Fusion HD Enzyme Premix 2 μL, reaction temperature 50° C., incubating for 15 min.

In this invention, said recombinant expression vectors are preferably verified before use. The method of said verification includes the following steps:

① transforming the recombinant expression vector into *E. coli* competent cell DH5a through thermal shock transformation, and then screening by using ampicillin;

② Performing bacterium shaking and plasmid extraction on the obtained bacterial plaque, saving the bacterial colony for PCR appraisal; there are T7 primer and infusion-nlea reverse primer in the upstream section of PYES2-NLEA; PCR appraisal is performed by taking the transformed plasmid as template to get the positive clone;

③ Sequencing the positive clone, alignment between the sequenced sequence and the original sequence is conducted, and the positive clones with a similarity of 100% is the successfully transformed recombinant *E. coli*.

This invention also provides a host containing said recombinant expression vectors.

In this invention, the host preferably includes *S. cerevisiae*, *E. coli* or *Agrobacterium*.

In this invention, the host containing said recombinant expression vectors has good salt tolerance in sodium chloride solution with molar concentrations within the range of 0.5 mol/L~0.8 mol/L.

In this invention, preferably, the preparation method of said host is transforming said recombinant expression vectors into the hosts.

In this invention, the method of said transformation is subject to no special restriction, and any common transformation methods known to a person skilled in the art can be used.

This invention also provides the use of said coding gene as selection marker in microorganism transgenic cell culture.

In this invention, said use as selection marker is specifically as follows: the transgenic cells or hosts are cultured under saline condition, only the cells or hosts with normal growth are successful transgenic material, and hosts without transformed salt tolerant protein cannot grow under saline condition.

An artificial salt tolerant protein, its synthetic method and coding gene thereof, and use of gene provided in this invention are described in detail below in combination with examples. However, these examples should not be understood as definition of the protection scope of this invention.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All headings are for the convenience of the reader and should not be used to limit the meaning of the text that follows the heading, unless so specified.

As used herein and in the appended claims, the singular forms "a," "an," and "the" include plural referents unless the context clearly dictates otherwise. For example, "a" or "an" means "at least one" or "one or more."

Example 1

Plasmid with synthesized gene determined by sequencing is taken as template, and the synthesized gene is also taken as template. The gene synthesized by the company is directly connected to puc57 vector which is made by the company itself, and this gene cannot exist alone. Amplification is conducted by using the positive primer shown in SEQ ID NO:3 and the reverse primer shown in SEQ ID NO:4, with the synthesized gene as template. The PCR amplification system is as follows: the total reaction system includes puc57-NLEA 1 μL, 5× phushion HF buffer 4 μL, 10 mmol/L dNTPs 0.4 μL, 10 μM gene specific primers 1 μL, Phusion DNA polymerase 0.2 μL, DMSO 0.6 μL, and the whole reaction volume is made up a deficiency by using 11.8 μL water. The PCR amplification procedure is: 98° C. 30 s; and taking 98° C. 10 s, 60° C. 30 s, 72° C. 1 min as one cycle, conducting 35 cycles; and finally 72° C. 5 min. The whole sample of 50 μL is applied for electrophoresis, and PCR products are reclaimed after agarose electrophoresis. puc57 vector in this example can be purchased.

Example 2

Double Enzyme Digestion on Vector PYES2

Plasmid PYES2 appraised by sequencing is taken as template, and SacI and EcoRI enzymes are used for the double enzyme digestion. The reaction system is as follows: 20,000 unit/ml SacI 1 μL, EcoRI 1 μL, 10× CutSmart 2.5 μL, PYES2 5 μL; the digestion temperature is preferably 50° C., with incubation 1 h; 65° C., with deactivation 15 min. The whole sample of 25 μL is applied for eletrophoresis, and digestion products are reclaimed after agarose electrophoresis.

FIG. 2 is a diagram of agarose gel electrophoresis of the vectors PYES2 after double enzyme digestion.

Example 3

Construction of Expression Vector PYES2-NLEA

The properly appraised gel extraction product of linearized plasmid PYES2 and the gel extraction PCR product of NLEA are connected by means of In-Fusion reaction. The reaction system is as follows: linearized vector PYES2 3 µL, PCR product 5 µL, 5× In-Fusion HD Enzyme Premix 2 µL, reaction temperature 50° C., incubating for 15 min.

The constructed recombinant expression vector is transformed into *E. coli* DH5a competent cell through thermal shock transformation, which specifically includes that, 2 µL connection product is transformed into 50 µL DH5α competent cell. The reactant is placed in ice bath for 30 min, thermal shock at 42° C. for 50 s, and placed onto ice quickly to keep for 2 min; 700 µL liquid LB culture media is added and shaken for 1 h at 37° C., 250 rpm. The reactant is centrifuged for 1 min at 5,000 rpm. The supernatant of 600 µL is removed, and the rest 150 µL is blown and sucked to suspend thalli. All the residual bacteria liquid is spread on solid LB plate containing 100 mg/ml Amp, to screen by ampicillin. Bacterium shaking and plasmid extraction for the bacterial plaque obtained by transformation are performed, and the bacterial colony is saved for PCR appraisal; there are T7 primer and infusion-nlea reverse primer in the upstream section of PYES2-NLEA, and PCR appraisal is performed by using the transformed plasmid as template. The positive clone is sequenced, and alignment between the sequencing result and the coding gene is conducted. Sequence of complete consistence indicates successful construction of PYES2-NLEA. FIG. 3 shows an expression vector containing salt tolerant coding gene NLEA.

Example 4

Transformation of Expression Vector pYES2-nlea into *S. cerevisiae*
1) 50 µL *S. cerevisiae* competent cells is melt on ice, and then 24, constructed recombinant vector is added.
2) 5 µL denatured linearized DNA is added into 50 µL PEG/LiAc, mixed up gently, and placed on ice for half an hour.
2) 20 µL DMSO is added into the mixture of step 1).
4) the reactant is placed to water bath for 15 min at 42° C.
5) high speed centrifugation 15 s.
6) the supernatant is discarded, and thalli are suspended with 1 ml YPD Plus, and shaken for 1 h at 30° C.
7) After high speed centrifugation for 15 s, the supernatant is discarded, and cells are suspended with 0.9% NaCl solution.
8) the bacteria solution is diluted with NaCl solution respectively by 10 times and 100 times.
9) 100 µL diluted bacteria solution is spread on auxotrophic culture medium SC-Ura.
10) being cultured for 3-5 days at 30° C., the positive clones are selected.

The auxotrophic culture medium is used to screen out whether the recombinant plasmid is successfully transformed into microzyme. As such culture media is uracil auxotrophic culture medium, and pYES2 contains uracil gene, only microzyme with successfully transcribed pYES2 can grow in this culture medium.

Example 5

Phenotype Appraisal of Transgenic Microzyme
*S. cerevisiae* with empty vector pYES2 (as control group) and *S. cerevisiae* with pYES2-nlea are respectively placed into selection culture medium with galactose induced liquid uracil, to observe their growth curve. If s shown from the observation results that, the *S. cerevisiae* with PYES2-NLEA had a better growth than the *S. cerevisiae* with empty vector PYES2. Then, high temperature sterilization is performed.

The growth conditions of the *S. cerevisiae* with empty vector PYES2 and *S. cerevisiae* with pYES2-nlea are observed after three days of growth (FIG. 4). If s shown from FIG. 4 that, *S. cerevisiae* with pYES2-nlea had significantly better growth than *S. cerevisiae* with empty vector pYES2 under the treatment condition of 600 mM NaCl.

Example 6

*S. cerevisiae* with empty vector pYES2 (as control group) and *S. cerevisiae* with pYES2-nlea are respectively placed into selection culture medium with galactose induced solid uracil. This culture medium includes salt treatments of different concentrations, respectively 0M, 0.1M, 0.2M, 0.3M, 0.4M, 0.5M, 0.6M, 0.7M, 0.8M, 0.9M and 1.0M.

Figure 5:
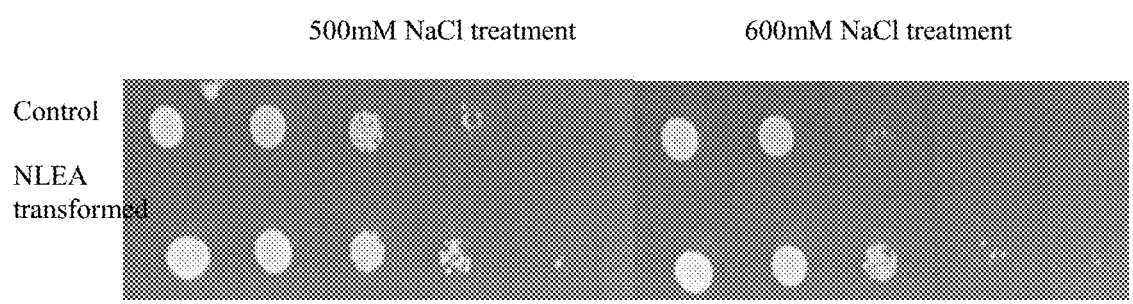
FIG. 5 shows phenotype observations of *S. cerevisiae* with NLEA transferred and wild strains under different salt stresses in example 6.

The phenotype of NLEA transformed *S. cerevisiae* and wild strains under different salt stresses are observed, and the phenotype observations of NLEA transformed *S. cerevisiae* and wild strains under different salt stresses are shown in FIG. 5. If s shown from FIG. 5 that, the salt tolerance of NLEA transformed *S. cerevisiae* in sodium chloride solution with molar concentrations of 0.5 mol/L and 0.6 mol/L is significantly different from that of the control group, and the highest salt tolerance of NLEA transformed *S. cerevisiae* is up to 0.8 mol/L NaCl.

Example 7

Plant expression vector pGWB14-NLEA which was constructed through Gateway technology was transformed into *Agrobacterium* GV3101 cells. Model plant of *Arabidopsis thaliana* were transfected by *Agrobacterium* GV3101 cells with pGWB14-NLEA transformed, and transgenic plants over-expressing nlea gene were then obtained by *Agrobacterium*-medicated transfection technology. Positive transfected plant were identified by kanamycin selective screen.

Figure 6:
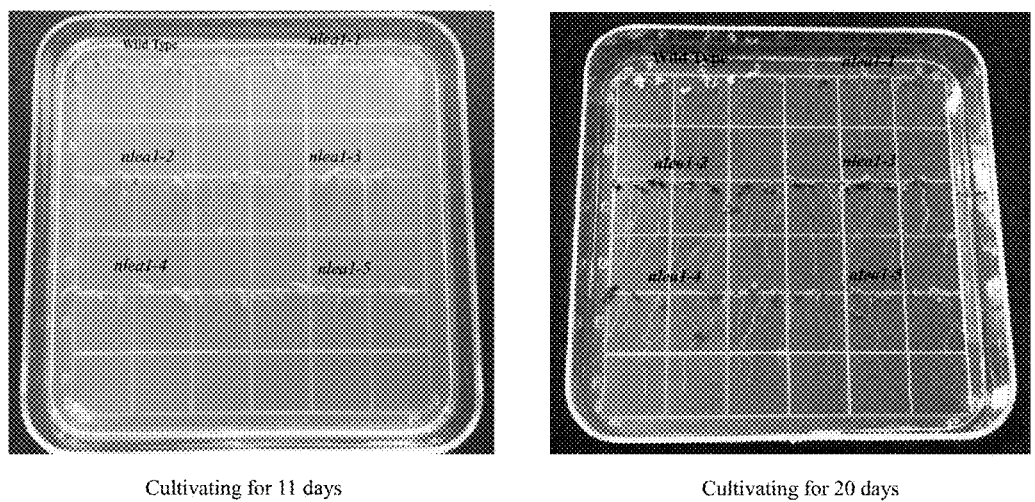
FIG. 6 shows observation on performance of wild-type *Arabidopsis thaliana* plant and transgenic *Arabidopsis thaliana* plant with nlea gene under salt stress with concentration of 100 m mol/L in example 7.

Wild type and transgenic *Arabidopsis* plants were sown on 1/2 MS solid media with different concentrations of NaCl as follows: 0 mM, 50 mM, 100 mM, 150 mM and 200 mM, and their growth under different salt stress were observed. It's shown by the observing results that, wild type plants turned to white, while transgenic plants stayed green after 20 days treatments. By transferring all plants to fresh 0 mM NaCl media, transgenic plants survived, while wildtype plants can't recover from salt treatments and all died (see FIG. 6).

The aforesaid embodiments are only preferred examples of present invention. It should be noted that a common person skilled in the art may make some improvements and modifications based on the principles of present invention. Such improvements and modifications should be deemed within the protection scope of present invention.

The invention claimed is:

1. An artificial salt tolerant protein NLEA, possessing the amino acid sequence shown as SEQ ID NO: 1.

2. A method of making said salt tolerant protein NLEA according to claim 1, comprising the following steps:
   1) retrieving different types of Late Embryogenesis Abundant (LEA) proteins from a LEA database;
   2) making multiple sequence alignments on the different types of LEA proteins retrieved in step 1) to obtain conserved short peptides;
   3) selecting hydrophilic short peptides with a hydrophilicity index higher than 3.5 from the conserved short peptides obtained in step 2);
   4) arranging and splicing the hydrophilic short peptides obtained in step 3) in the order of isoelectric point size from large to small, to get the salt tolerant protein NLEA; wherein the amino acid sequence of said salt tolerant protein NLEA is shown as SEQ ID NO: 1;
   5) synthesizing the sequence of a nlea gene of the NLEA protein by polymerase chain reaction (PCR), connecting said sequence of the nlea gene into a PYES2 vector to construct an expression vector PYES2-NLEA, in order to express the NLEA protein; wherein said sequence of the nlea gene is shown as SEQ ID NO: 2.

3. The method according to claim 2, wherein the hydrophilicity index of step 3) is calculated by using the Formula I below:

$$\text{hydrophilicity index} = \frac{\sum_{i=1}^{n} f(i)}{n} \quad \text{formula I}$$

f(i) is the hydrophilicity number of single amino acid; n=11.

4. The method according to claim 2, further comprising the step of making a clustering analysis of said conserved short peptides before selecting the hydrophilic short peptides in said step 3), to get the conserved short peptides clustering in different branches.

5. A gene coding the salt absorbent protein NLEA according to claim 1, comprising a nucleotide sequence of SEQ ID NO: 2.

6. A recombinant expression vector comprising the gene of claim 5.

7. The recombinant expression vector according to claim 6, characterized in that, said recombinant expression vector is pYES2-nlea.

8. A host comprising the recombinant expression vector according to claim 6.

9. The host according to claim 8, wherein said host comprises *S. cerevisiae, E. coli* or *Agrobacterium*.

10. A method of using the gene according to claim 5 as a selection marker in microorganism transgenic cell culture comprising the step of culturing transgenic cells or host cells under saline conditions.

11. A host comprising the recombinant expression vector according to claim 7.

* * * * *

SEQUENCE LISTING

<160> NUMBER OF SEQ ID NOS: 5

<210> SEQ ID NO 1
<211> LENGTH: 110
<212> TYPE: PRT
<213> ORGANISM: Artificial Sequence
<220> FEATURE:
<223> OTHER INFORMATION: Artificial salt tolerant protein NLEA which is
      artificially synthesized

<400> SEQUENCE: 1

Arg Glu Glu Glu Glu Gln Arg Arg Gln Arg Arg Arg Glu Glu Glu Glu
1               5                   10                  15

Gln Arg Arg Gln Arg Arg Arg Glu Glu Glu Glu Gln Arg Arg Gln Arg
            20                  25                  30

Arg Arg Glu Glu Glu Glu Gln Arg Arg Gln Arg Arg Arg Glu Glu Glu
        35                  40                  45

Glu Gln Arg Arg Gln Arg Arg Arg Glu Glu Glu Glu Gln Arg Arg Gln
    50                  55                  60

Arg Arg Arg Glu Glu Glu Glu Gln Arg Arg Gln Arg Arg Arg Glu Glu
65                  70                  75                  80

Glu Glu Gln Arg Arg Gln Arg Arg Arg Glu Glu Glu Glu Gln Arg Arg
                85                  90                  95

Gln Arg Arg Arg Glu Glu Glu Glu Gln Arg Arg Gln Arg Arg
            100                 105                 110

<210> SEQ ID NO 2
<211> LENGTH: 336
<212> TYPE: DNA
<213> ORGANISM: Artificial Sequence
<220> FEATURE:
<223> OTHER INFORMATION: Gene nlea of Artificial salt tolerant protein
      NLEA which is artificially synthesized

<400> SEQUENCE: 2
atgagagaag aagaggaaca aagaagacaa aggcgtagag aggaagagga acagaggcgt      60
caaagaagga gagaggaaga agaacagaga aggcaaagga gaagggaaga agaggagcaa     120
agaaggcaaa gacgtaggga agaagaagag caaaggagac agaggaggcg tgaagaagaa     180
gaacaaagaa gacaacgtag aagggaagag gaagaacaaa gacgtcagag aagacgtgag     240
gaagaagagc agagaagaca aagacgtcgt gaagaggaag agcagagaag acaaagaaga     300
agagaagaag aagaacaacg tagacaaagg agatag                               336

<210> SEQ ID NO 3
<211> LENGTH: 20
<212> TYPE: DNA
<213> ORGANISM: Artificial Sequence
<220> FEATURE:
<223> OTHER INFORMATION: Forward Primer of Gene nlea which is
      artificially synthesized

<400> SEQUENCE: 3
ttaagcttgg taccgagctc                                                  20

<210> SEQ ID NO 4
<211> LENGTH: 16
<212> TYPE: DNA
<213> ORGANISM: Artificial Sequence
<220> FEATURE:
<223> OTHER INFORMATION: Reverse Primer of Gene nlea which is
      artificially synthesized

```
<400> SEQUENCE: 4
gatatctgca gaattc                                              16

<210> SEQ ID NO 5
<211> LENGTH: 22
<212> TYPE: DNA
<213> ORGANISM: Artificial Sequence
<220> FEATURE:
<223> OTHER INFORMATION: T7 primer which is artificially synthesized

<400> SEQUENCE: 5
cgtaatacga ctcactatag gg                                       22
```